US00PP30575P2

(12) United States Plant Patent
Kordes

(10) Patent No.: US PP30,575 P2
(45) Date of Patent: Jun. 18, 2019

(54) MINIATURE ROSE PLANT NAMED 'KORPOT078'

(50) Latin Name: *Rosa hybrida*
Varietal Denomination: KORpot078

(71) Applicant: W. KORDES' SÖHNE Rosenschulen GmbH & Co. KG, Klein Offenseth-Sparrieshoop (DE)

(72) Inventor: Wilhelm-Alexander Kordes, Klein Offenseth-Sparrieshoop (DE)

(73) Assignee: W. KORDES' SOHNE ROSENSCHULEN GMBH & CO. KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 15/732,567

(22) Filed: Nov. 29, 2017

(30) Foreign Application Priority Data

Oct. 18, 2017 (QZ) ..... PBR 2017/2619

(51) Int. Cl.
*A01H 5/02* (2018.01)

(52) U.S. Cl.
USPC ..... Plt./120

(58) Field of Classification Search
USPC ..... Plt./120
See application file for complete search history.

(56) References Cited

U.S. PATENT DOCUMENTS

PP19,598 P2 12/2008 Kordes
PP20,233 P3 * 8/2009 White ..... Plt./120
PP25,004 P2 10/2014 Kordes

* cited by examiner

*Primary Examiner* — Annette H Para
(74) *Attorney, Agent, or Firm* — Buchanan Ingersoll & Rooney PC

(57) ABSTRACT

A new and distinct variety of Miniature Rose Plant, herein referred to by its cultivar name, 'KORpot078', is provided which forms in abundance on a substantially continuous basis attractive, salmon pink colored blossoms. The vegetation is vigorous and the growth habit is compact. Attractive ornamental foliage is formed with good disease resistance. The new variety is particularly well suited for providing distinctive ornamentation in the landscape.

2 Drawing Sheets

CROSS-REFERENCE TO RELATED APPLICATIONS

Figure 1:
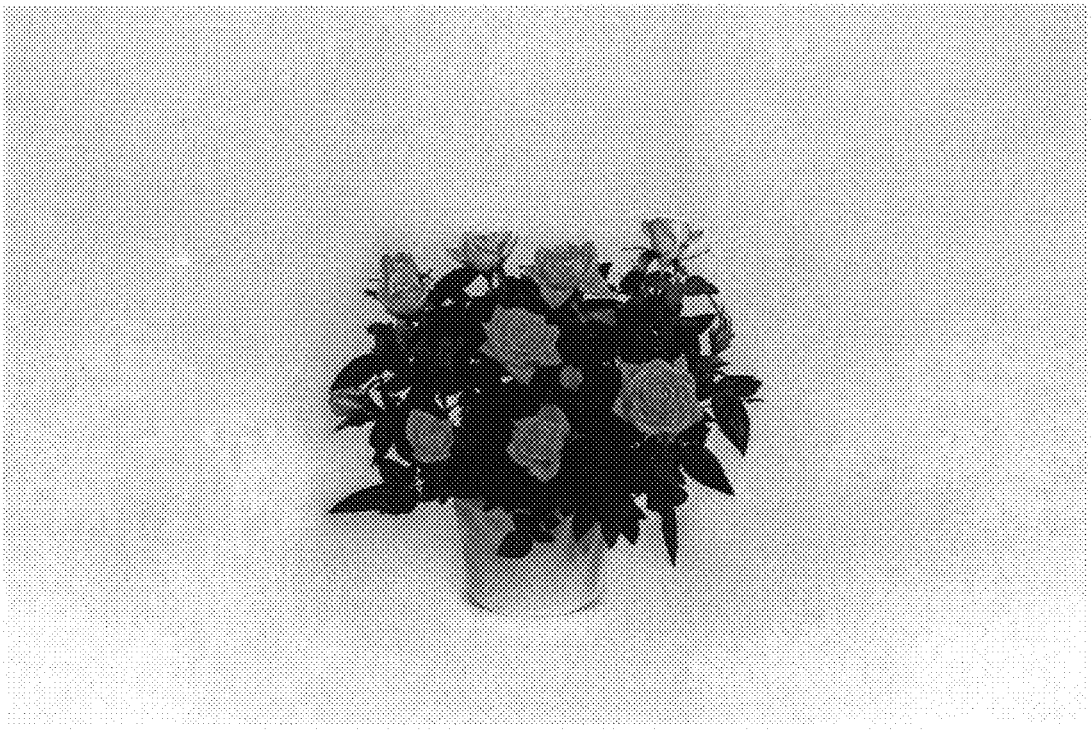

This application claims priority to Plant Breeders' Right Application Number 2017/2619, which was filed at Community Plant Variety Office in the European Union on Oct. 18, 2017, the contents of which are hereby incorporated by reference for all purposes.

Botanical/commercial classification:
Latin name—*Rosa hybrida.*
Common name—Miniature Rose Plant.
Varietal denomination: 'KORpot078'.

SUMMARY OF THE INVENTION

The new variety of *Rosa hybrida* Miniature Rose Plant of the present invention was created during 2013 at Offenseth-Sparrieshoop, Germany by artificial pollination wherein two parents were crossed which previously had been studied in the hope that they would contribute the desired characteristics. The female parent (i.e., seed parent) of the new variety was the 'KORhedani' variety (U.S. Plant Pat. No. 19,598). The male parent (i.e., pollen parent) was the 'KORpot028' variety (U.S. Plant Pat. No. 25,004).

The parentage can be summarized as follows:

'KORhedani' x 'KORpot028'

The seeds resulting from the above pollination were sown and small plants were obtained which were physically and biologically different from each other. Selective study resulted in the identification of a single plant of the new variety.

It was found that the new Miniature Rose Plant of the present invention possesses the following combination of characteristics:

(a) abundantly and substantially continuously forms attractive, salmon pink colored blossoms,
(b) exhibits a compact growth habit,
(c) forms vigorous vegetation, and
(d) forms attractive ornamental foliage with good disease resistance.

The new variety well meets the needs of the horticultural industry. It can be grown to advantage as ornamentation in parks, gardens, public areas, and in residential settings. Accordingly, the plant is particularly well suited for growing in the landscape.

The new variety can be readily distinguished from its ancestors. More specifically, the 'KORhedani' variety (i.e., seed parent) exhibits a different flower color than the new variety and displays solitary flowers, whereas the new variety forms clusters of flowers and has an improved shelf life compared to the 'KORhedani' variety. Additionally, the 'KORnilsca' variety (i.e., pollen parent) exhibits a different flower color, a larger flower size, and less compact habit than that of the new variety. Moreover, the new variety can be readily distinguished from non-parental related similar varieties. For example, the 'KORpot050' variety (U.S. Plant Pat. No. 27,162) provides orange-red colored blossoms and displays more pointed flower shape and more vigor growth habit compared to the new variety, whereas the new variety provides salmon-pink colored blossoms. In addition, the 'SAVasleep' variety (U.S. Plant Pat. No. 20,233) exhibits a moderate to strong, sweet fragrance and displays an upright and spreading growth habit, whereas the new variety exhibits a very light, sweet fragrance and displays a very bushy and compact growth habit.

The new variety has been found to undergo asexual propagation in Klein Offenseth-Sparrieshoop, Germany by a number of routes such as vegetative cuttings. Asexual propagation techniques in Germany have shown that the characteristics of the new variety are homogeneous, stable, and strictly transmissible by such asexual propagation from one generation to another. Accordingly, the new variety undergoes asexual propagation in a true-to-type manner.

The new variety has been named 'KORpot078'.

BRIEF DESCRIPTION OF THE PHOTOGRAPHS

The accompanying photographs show, as nearly true as it is reasonably possible to make the same in color illustrations of this character, a typical specimen of the new variety. The illustrated rose plant of the new variety was approximately twelve weeks of age and was observed at Klein Offenseth-Sparrieshoop, Germany while growing indoors on its own roots in a 6 cm container.

FIG. 1—illustrates a specimen of a plant displaying floral buds and flowers at varying points of opening.

Figure 2:
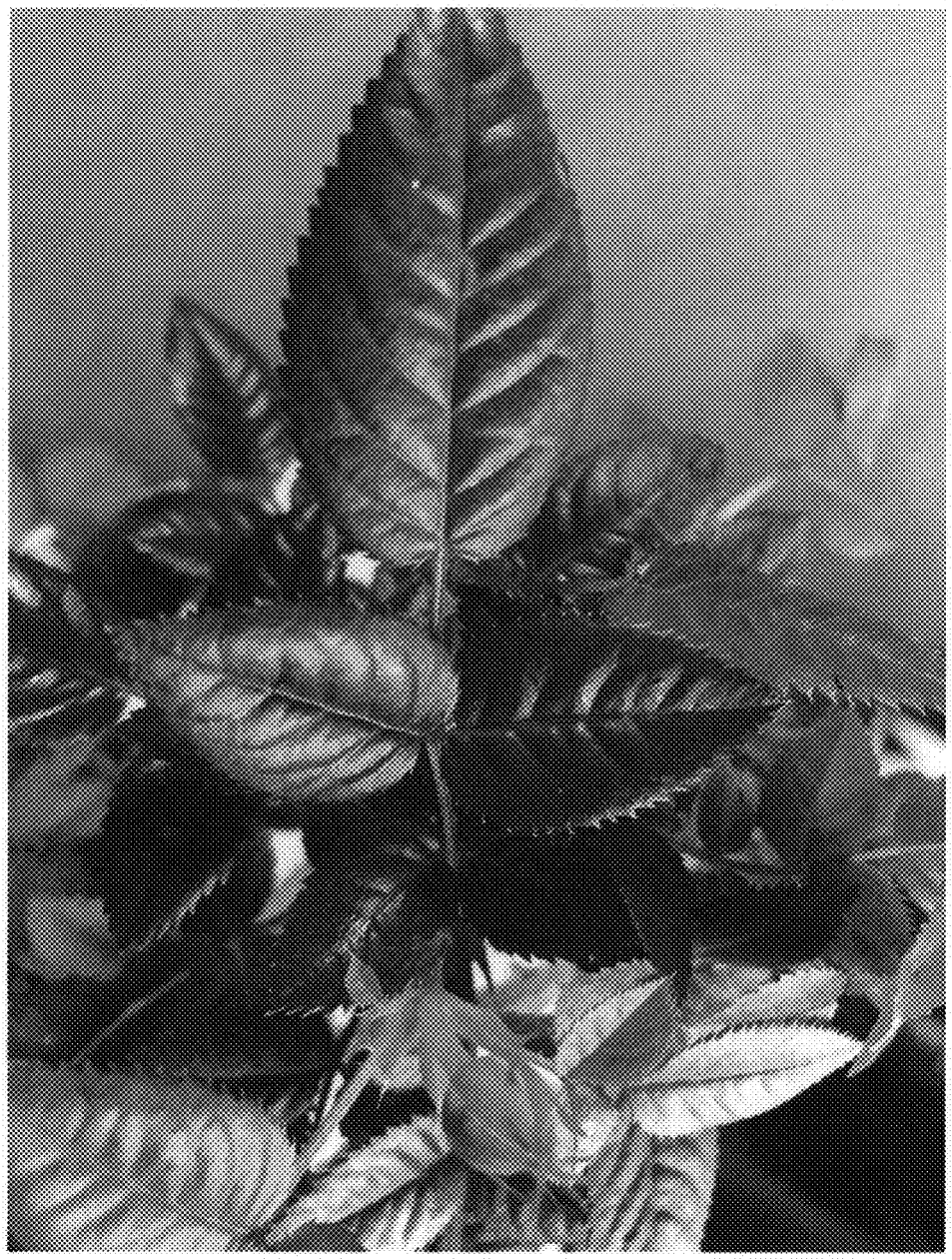

FIG. 2—illustrates specimen of the foliage—plane view—obtuse.

DETAILED BOTANICAL DESCRIPTION

The chart used in the identification of colors is that of The Royal Horticultural Society (R.H.S. Colour Chart, 2015 edition). The terminology which precedes reference to the chart has been added to indicate the corresponding color in more common terms. The description is based on the observation of a one-year-old specimen of the new variety, observed during July, while growing in a one-gallon container on its own roots at Cochranville, Pa.

Class: Miniature Rose Plant.

Plant:

*Habit*.—Very bushy and compact.

*Height*.—Approximately 18.0 cm on average.

*Width*.—Approximately 33.0 cm on average.

Branches:

*Stem color*.—Commonly near Yellow-Green Group 144A.

*Main stem length*.—Approximately 18.0 cm on average.

*Secondary stem length*.—Approximately 6.0 cm on average.

*Surface texture*.—Mature stems are smooth; immature stems are smooth.

*Thorns*.—Number: approximately 8 throns per 6.0 cm of stem length, on average. Young thorns: length is approximately 4.0 mm on average, width is approximately 1.0 mm at point of attachment on average, amount is moderate, and color is commonly near Yellow-Green Group 145C. Old thorns: length is approximately 4.0 mm on average, width is approximately 1.0 mm at point of attachment on average, amount is moderate, and color is commonly near Greyed-Orange Group 177B.

Foliage:

*General appearance*.—Ornamental with good disease resistance.

*Young foliage*.—Upper surface color: commonly near Green Group 137A. Under surface color: commonly near Green Group 137C with some interveinal tones of near Greyed-Orange Group 176A.

*Old foliage*.—Upper surface color: commonly near Green Group NN137A. Under surface color: commonly near Green Group 138B.

*Petiole*.—Upper surface: texture is smooth, color is commonly near Green Group NN137A. Under surface: texture is smooth, color is commonly near Green Group 138B. Length: approximately 2.0 cm on average.

*Rachis*.—Color: upper surface is commonly near Green Group 137B, under surface is commonly near Green Group 143B. Size: length is approximately 5.5 cm on average. Surface texture: smooth with a few small prickles on the under surface.

*Stipules*.—Length: approximately 17.0 mm on average. Width: approximately 6.0 mm on average. Margin: entire to erose. Color: upper surface is commonly near Green Group 137C with intonations of near Greyed-Red Group 178B towards the margin; lower surface is commonly near Green Group 137D with intonations of near Greyed-Red Group 178B towards the margin.

*Leaf margin*.—Serrate.

*Leaf arrangement*.—Odd pinnate.

Leaflets:

*Number*.—3, 5, and 7.

*Shape*.—Ovate.

*Venation*.—Type is reticulate and color is commonly near Green Group 143A.

*Texture*.—Upper surface is smooth; lower surface is smooth.

*Size*.—Terminal leaflet: length is approximately 4.5 cm on average; width is approximately 2.2 cm on average. Lower leaflets: length is approximately 2.2 cm on average and width is approximately 1.5 cm on average. 5-Leaflet leaf: length is approximately 9.5 cm on average and width is approximately 6.0 cm on average.

*Terminal leaflet general*.—Glossiness intensity of upper surface is moderate; margin undulation is absent; apex shape is acute; base shape is rounded.

Inflorescence:

*Number of flowers*.—Approximately 10 blooms on average on a plant at once.

*Number of blooms per stem or in a cluster*.—Commonly between 1 and 5 blooms per stem on average.

*Type*.—Solitary.

*Size*.—Length is approximately 5.5 cm on average; and width is approximately 5.5 cm on average.

*Peducle*.—Color: commonly Yellow-Green Group 144A. Diameter: approximately 3.0 mm on average. Length: approximately 2.0 cm on average. Surface texture: smooth.

*Sepals*.—Number: commonly 5. Upper surface color and texture: covered in short pubescence and color is commonly near Yellow-Green Group 144A. Under surface color and texture: puberulent and color is commonly near Yellow-Green Group 144B. Size: length is approximately 2.5 cm on average and width is approximately 7.0 mm on average. Shape: lanceolate; apex is acute to aristate. Margin: entire with occasional extensions on two or three sepals measuring approximately 5.0 mm in length and approximately 1.0 mm in width.

*Bud*.—Shape: ovoid. Size: length is approximately 1.8 cm on average; width is approximately 1.5 cm on average. Color (when opening): commonly near Red Group 39B.

*Flower*.—Salmon pink colored. Form: double, cuplike Shape: rounded. Diameter: approximately 5.5 cm on average. Height: approximately 2.5 cm on average. Duration: commonly on the plant approximately 20 days. Color upper and under surfaces upon opening/after opening/fully open: commonly near Red Group 38A with an inner blotch of near White Group NN155 and near Yellow Group 12C at the point of attachment; basal spot is commonly near White Group NN155A.

*Fragrance*.—Very light sweet fragrance.

*Petal*.—Number: approximately 60 on average. Drop: good. Length: inner petals are approximately 1.6 cm on average; outer petals are approximately 2.3 cm on average. Width: inner petals are approximately 1.2 cm on average; outer petals are approximately 2.3 cm on average. Shape: overall shape is broadly obovate; apex is round; and base is cuneate. Texture: upper and under surface is glabrous. Margin: entire; margin undulation is weak to moderate.

*Petaloids*.—Number: approximately 6-8 per flower, on average. Color upper surface upon opening/after opening/fully open: commonly near Red Group 41C transitioning to near Yellow Group 12C at the point of attachment. Color under surface upon opening/after opening/fully open: commonly near Red Group 39B with intonations of near Yellow-White Group 158B through the centeral portions and through the point of attachment. Basal spot: color is commonly near White Group NN155A. Length: approximately 1.0 cm on average. Width: approximately 8.0 mm on average. Texture: smooth. Margin: variable, entire to erose. Shape: variable, oblong and mostly curving inward; apex is round; base is cuneate.

*Stamen*.—Number: approximately 95 on average. Anthers: number is about 95 and color is commonly near Yellow-Orange Group 20A; length is approximately 6.0 mm on average. Filaments: length is approximately 2.0 mm on average and color is commonly near Yellow Group 11A.

*Pistils*.—Arrangement: separate and free. Number: approximately 130. Style: color is commonly near Red Group 39A toward the apex, transitioning to Green-White Group 157D at the base; length is approximately 3.0 mm on average. Stigma: color is commonly near Greyed-Yellow Group 160A with some blending of near Red Group 39A; diameter is commonly less than 1.0 mm on average.

*Receptacle*.—Achenes stand on the bottom and wall; diameter is approximately 1.0 cm on average, shape is round, color Is commonly near Yellow-Green Group 144A, and surface texture is smooth.

*Pollen*.—None observed.

*Hips*.—None observed.

Development:

*Vegetation*.—Dark green, vigorous, and strong.

*Hardiness zone*.—Unknown.

*Blooming*.—Abundant and substantially continuous.

*Resistance to diseases*.—Good resistance to Powdery mildew (*Sphaerotheca pannosa*) and *Botrytis* (*Botrytis cinerea*) diseases under normal greenhouse growing conditions in Cochranville, Pa.

Plants of the 'KORpot078' variety have not been observed under all possible environmental conditions to date. Accordingly, it is possible that the phenotypic expression may vary somewhat with changes in light intensity and duration, cultural practices, and other environmental conditions.

I claim:

1. A new and distinct Miniature Rose Plant characterized by the following combination of characteristics:

(a) abundantly and substantially continuously forms attractive, salmon pink colored blossoms, (b) exhibits a compact growth habit, (c) forms vigorous vegetation, and (d) forms attractive ornamental foliage with good disease resistance; substantially as herein shown and described.

* * * * *